(12) United States Patent
Skalak et al.

(10) Patent No.: US 6,607,495 B1
(45) Date of Patent: Aug. 19, 2003

(54) APPARATUS FOR FLUID TRANSPORT AND RELATED METHOD THEREOF

(75) Inventors: Thomas C. Skalak, Afton, VA (US); Patrick S. Cottler, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 40 days.

(21) Appl. No.: 10/009,886

(22) PCT Filed: Jun. 19, 2000

(86) PCT No.: PCT/US00/16880
§ 371 (c)(1),
(2), (4) Date: Dec. 12, 2001

(87) PCT Pub. No.: WO00/78212
PCT Pub. Date: Dec. 28, 2000

Related U.S. Application Data

(60) Provisional application No. 60/140,137, filed on Jun. 18, 1999, and provisional application No. 60/172,290, filed on Dec. 17, 1999.

(51) Int. Cl.[7] ............................. A61B 5/00; B65D 81/00
(52) U.S. Cl. ......................................... 600/573; 604/19
(58) Field of Search ............................. 600/573, 576, 600/578, 580, 583; 604/19, 22, 35; 606/181, 182, 183

(56) References Cited

U.S. PATENT DOCUMENTS

| | | | |
|---|---|---|---|
| 3,741,197 A | 6/1973 | Sanz et al. | |
| 3,742,954 A | 7/1973 | Strickland | |
| 4,462,405 A | 7/1984 | Ehrlich | |
| 4,781,700 A | * 11/1988 | Vicario | ........................ 604/234 |
| 5,582,184 A | 12/1996 | Erickson et al. | |
| 5,680,872 A | 10/1997 | Sesekura et al. | |
| 5,879,367 A | 3/1999 | Latterell et al. | |
| 6,032,059 A | * 2/2000 | Henning et al. | ............ 600/345 |
| 6,071,267 A | 6/2000 | Zamierowski | |
| 6,183,434 B1 | * 2/2001 | Eppstein | ...................... 604/22 |

OTHER PUBLICATIONS

P. S. Cottler et al.,Design and Test of Clinically Relevant Treatments for Venous Congested Skin Flaps in an Animal Model, presentation: 2nd Conf. on the Development of Tech. in Med. for VA, Nov. (1999).

(List continued on next page.)

Primary Examiner—Max F. Hindenburg
Assistant Examiner—Jonathan Foreman
(74) Attorney, Agent, or Firm—Robert J. Decker

(57) ABSTRACT

The fluid transport apparatus and related method for withdrawing fluid from, or infusing fluid to, a target. The apparatus has a fluid collection chamber that has attached thereto cutting devices. The cutting devices are used to make incisions through the wall or skin of the body or target by inserting the cutting device or devices through the wall of the body for automatically removing blood or other tissue fluids from the skin or other tissues. In the operating mode, the motion of the actuator from the rest position to a displaced position generates a negative pressure in the fluid collection chamber that draws blood or fluid from the target into the collection chamber.

47 Claims, 10 Drawing Sheets

OTHER PUBLICATIONS

P.S. Cottler et al., Eval. of Clinically Applicable Exsanguination Treatments to Alleviate Venous Congestion in a RAT Skin Flap Model, Presented: 3rd Joint Mtg of the EU Tissue Repair Society & the Wound Healing Society, Aug. (1999).

Tamburo, R.J. et al., Microvascular Network Modeling and Simulated Hemodynamics of a Rat Skin Flap, Presented NIGMS/National Minority Research Symposium, Nov. (1998).

Cottler, P.S. et al., Microvascular Network Anatomy and Hemodynamic Simulation of a Rat Pedicle Skin Flap, Ann. Biomed. 25 Suppl I: 300, (1997).

Reuters, CNN.com/HEALTH, Mechanical Leech Does Icky Job Better, created Dec. 15, 2001, http://www.cnn.com/2001/HEALTH/12/15/leech.mechanical.reut/index.html.

P.S. Cottler et al., Evaluation of Clinically Applicable Exsanguination Treatments to Alleviate Venous Congenstion in an Animal Skin Flap Model, Wound Repair and Regeneration, vol. 7. No. 3, pp 187–195, (1999).

Lauren Gravitz, Follow Up: A Better Bloodsucker, Discover, vol. 23, No. 3, pp. 16, Mar. (2002).

Smoot, et al., Mechanical Leech Therapy to Relieve Venous Congestion, Journal of Reconstructive Microsurgery, vol. 11, No. 1, Jan. (1995).

* cited by examiner

APPARATUS FOR FLUID TRANSPORT AND RELATED METHOD THEREOF

CROSS-REFERENCES TO RELATED APPLICATIONS

The present invention claims priority from U.S. Provisional Patent Application Serial No. 60/1140,137 filed Jun. 18, 1999, entitled "Disposable Device for Biological Fluid Transport," and 60/172,290 filed Dec. 17, 1999, entitled "Disposable Device for Biological Fluid Transport," the entire disclosures of which are hereby incorporated by reference herein.

FIELD OF THE INVENTION

The present invention relates generally to an apparatus and method thereof for withdrawing fluids, and more particularly to an apparatus and method capable of percutaneous or direct removal of blood and other body fluids.

BACKGROUND OF THE INVENTION

Reconstructive and plastic surgery often involves the transfer of tissue to deep defects, where skin grafts would not be beneficial. During such transfer, the harvested tissue is without blood flow. If the blood flow is not restored quickly, due to microvascular complications, part or all of the tissue may become necrotic and the skin flap will fail. One such complication, venous congestion, involves inadequate venous drainage with a patent arterial inflow, and is due to tissue edema, venous thrombosis, leukocyte aggregation, or the fact that in some cases, microvascular reconnections of the venules are not surgically possible.

By way of background, skin flaps are a common feature utilized by plastic surgeons to reconstruct defects and to cover deep wounds in which a skin graft or replacement is not feasible because a patent vascular bed is absent. A skin flap is a multi-layered tissue that includes dermis, epidermis, subcutaneous tissue, fasciocutaneous, myocutaneous, osseocutaneous, and sometimes muscle tissue, sensory tissue, and possibly underlying adipose tissue, which is based on its own microvascular network. There are many thousands of cases each year that require the use of skin flaps to some degree during a medical procedure whereby these procedures can cost thousands of dollars. Reconnection of arteries to establish adequate arterial flow is vital for the ultimate success of these microsurgical procedures.

Nonetheless, skin flaps with proper arterial flow can still have compromised venous outflow, known as venous congestion, for a variety of reasons. Venous insufficiency has adverse effects, and leads to a majority of the failures in replantation surgeries. Venous congestion is a clinical problem in which extensive effort has been spent in attempts to alleviate or prevent its onset.

As a result, fluid transport techniques such as medicinal leeches are used as a treatment option in these cases to promote nutritive blood flow. The medicinal leech is currently used to initiate blood flow and reduce tissue swelling in skin grafts or replanted digits, and to promote nutritive blood flow. The medicinal leech attaches to its host utilizing three semicircular jaws containing approximately sixty (60) pairs of cutting teeth to create a "Y" shaped incision 1 to 2mm in diameter. Once attached, the bioactive saliva is secreted between each pair of teeth, and the nervous system stimulates the pharynx to pump peristaltically, creating a negative pressure, which aids in driving blood flow into the leech. Leeches will feed until stretch receptors are stimulated by distention in the body. It has been reported that feeding on large mammals, if allowed to proceed undisturbed, will last from 20 to 60 minutes, in which time the leech will ingest 5 to 15 ml, which is up to ten times the initial body weight. Once detached, the bite wound will continue to bleed, which is thought to be an important portion of the therapy. The wound will "ooze" up to 50 ml more in the 24 to 48 hours after feeding. In order for this secondary part of the treatment to be effective, the wound must be continuously cleared of thromboses that form on the patient's skin surface.

The use of leeches establishes a zero or negative pressure outlet for several vessels in the congested area. With the outlet, flow can resume at a basal level, supplying minimal necessary nutrients to the flap. If the flap can survive long enough due to this artificial flow, vessel reconnections can form, leading to survival of the flap.

As stated previously, one of the major factors in a successful tissue transplantation or replantation is the reestablishment of blood flow. The most common cause of flap failure is venous insufficiency, which can be treated with the use of medicinal leeches. However, the use of leeches carries the risk of infection and offers poor flow control. Potential problems for the patient that can arise with the use of the medicinal leech range from psychological problems, such as fear and disgust, to pharmacological problems in nature. Once a patient is comfortable with the procedure, there are other potential problems that can arise. Leeches rely on bacterium for the digestion of the ingested blood, due to the lack of proteolytic enzymes within the gut. One such bacteria is Aeromonas hydrophilia, a gram-negative rod, which has led to seprcaemia, pneumonia and gastroenteritis in humans. These bacteria may be ejected into the patient and cause infection. Infection rates of up to 20 percent have been linked to A-hydrophilia from leeches. Some patients experience anaphylaxis and allergic responses to the bioactive saliva of leeches, while others exhibited excessive scarring from the bite wound site. Continued leech use and persistent bleeding from the wound can result in a significant loss in blood volume. Hemoglobin levels can drop by 1 to 2 gm percent over a five day treatment due to the amount of blood lost, thus requiring a blood transfusion. Finally, if the leech is not monitored, it may wander to a more perfused region of the body to initiate feeding, rendering the treatment useless. Leeches are a widely used clinical tool today as evidenced by Biopharm Ltd. marketing 50,000 leeches per year, while Leeches USA Ltd. typically supplies 20,000 leeches per year. Due to these potential shortcomings of medicinal leeches, alternative methods to leech treatments would be very important to the future of microsurgery.

An alternative approach to medicinal leeches is a mechanical leech disclosed by Smoot in an article entitled "Mechanical Leech Therapy to Relieve Venous Congestion." It appears that the Smoot device is arranged with an elongated suction chamber with an inflow port for heparinzed saline and an outflow port for continuous suction. In operating mode, the Smoot-device is placed over a biopsy wound measuring 4 mm in diameter and suction is adjusted to achieve a negative pressure.

While the Smoot device appears to overcome some of the psychological and pharmacological failings of traditional medicinal leeching, as it attempts to replace a natural leech, it nevertheless has its own shortcomings. In this regard one shortcoming of the Smoot device is that it is not self-contained. Another major shortcoming relative to the present invention is that the suction pressure of the Smoot device is extremely large (i.e., −80 mmHg), and can not be varied cyclically. Cyclic variations are useful to maintain good flow and prevent blood clotting and/or clogging of channels. Such a large negative pressure, as required by the Smoot device, could collapse blood vessels and compact tissue, leading to clogging of transport channels. Another shortcoming of the Smoot device is that the outlet size of the biopsy wound is much greater than the required insertion of the present invention and could even be considered a wound that is detrmental to the patient A further shortcoming of the Smoot device is that the flow of heparinized saline leads to the susceptibility of spillage. An additional shortcoming of the Smoot device is that the device itself is not contained within a self-powered unit. The Smoot device is also unlikely to work on a clinically venous congested flap. A final shortcoming of the Smoot device is that a punch biopsy is required in the flesh of the subject prior to the "leech" being used, and consequently an increased risk of contamination. Clinicians have previously used skin excisional wounds(large area wounds) to treat seriously coagulated skin flaps. So the Smoot device essentially adjusts suction to a large area wound and would not be effective for venous congested flaps.

There is therefore a need in the art for an effective mechanical leech apparatus for percutaneous or direct removal of blood and other body fluids which does not suffer the disadvantages associated with a medicinal leech and/or conventional mechanical leeching methods.

SUMMARY OF THE INVENTION

A novel approach for withdrawing or infusing fluids, and more particularly to an apparatus and method capable of percutaneous or direct removal of blood and other body fluids, or infusion of medicinal, therapeutic, bioactive mixtures.

In one aspect, the present invention features a fluid transport apparatus for withdrawing fluid from a target, the fluid transport apparatus comprising: at least one fluid collection chamber having a target wall and a distal wall opposite of the target wall, whereby the target wall is adapted for being mated against the target while the transport apparatus is in use; an actuator means that at least partially forms a portion of the distal wall, the actuator means reciprocates when activated; at least one cutting device attached to the target wall of the fluid collection chamber and extending away from the fluid collection chamber, each such cutting device having at least one passage for transporting fluid there through; and a power supply operatively connected to the actuator means for activating the actuator, the actuator means reciprocates in an upward and downward motion relative to the target when activated, whereby the upward motion expands the volume of the collection chamber to provide a negative pressure in the fluid collection chamber relative to the pressure of the target whereby the negative pressure causes the fluid to be transported from the target into the fluid collection chamber.

In another embodiment the present invention features a fluid transport apparatus for withdrawing fluid from a target, the fluid transport apparatus comprising: at least one air storage chamber having an intermediate wall and a distal wall opposite of the intermediate wall; at least one fluid collection chamber having a wall that is defined by the intermediate wall, the collection chamber further including a target wall opposite of the intermediate wall, whereby the target wall is adapted for being mated against the target while the transport apparatus is in use; an actuator means that is in mechanical communication with the distal wall, the actuator means reciprocates when activated; at least one cutting device attached to the target wall of the fluid collection chamber and extending away from the fluid collection chamber, each such cutting device having a passage for transporting fluid there through; and a power supply operatively connected to the actuator means for activating the actuator means, the actuator means reciprocates causing the distal wall to reciprocate in an upward and a downward motion relative to the target when activated, whereby the upward motion expands the volume of the air storage chamber to provide a negative, pressure in the air storage chamber and fluid collection chamber relative to the pressure of the target and whereby the negative pressure causes the fluid to be transported from the target into the fluid collection chamber.

In another embodiment the present invention features a detachable fluid transport apparatus for withdrawing fluid from a target, the detachable fluid transport apparatus comprising a first section that is in communication with and detachable from a second section, the apparatus comprising: an attachment means that fastens the first and second sections so as to be in communication with one another and to be detachable from one another. Wherein the first section comprises: at least one fluid collection chamber having a target wall and a distal wall opposite of the target wall, whereby the target wall is adapted for being mated against the target while the transport apparatus is in use; and at least one cutting device attached to the target wall of the fluid collection chamber and extending away from the fluid collection chamber, each such cutting device having a passage for transporting fluid there through. Wherein the second section comprises: an actuator means that is in mechanical communication with the distal wall; and a power supply operatively connected to the actuator means for activating the actuator means, the actuator means reciprocates causing the distal wall to reciprocate in an upward and a downward motion relative to the target when activated, whereby the upward motion expands the volume of the air storage chamber to provide a negative pressure in the air storage chamber and fluid collection chamber relative to the pressure of the target and whereby the negative pressure causes the fluid to be transported from the target into the fluid collection chamber.

Another embodiment of the present invention is a fluid transport apparatus for infusing fluid into a target, the fluid transport apparatus comprising: at least one fluid dispenser chamber having a target wall and a distal wall opposite of the target wall, whereby the target wall is adapted for being mated against the target while the transport apparatus is in use; an actuator means that is in mechanical communication with the distal wall, the actuator means reciprocates when activated; at least one cutting device attached to the target wall of the fluid dispenser chamber and extending away from the fluid dispenser chamber, each such cutting device having a passage for transporting fluid there through; and a power supply operatively connected to the actuator means for activating the actuator, the actuator means reciprocates in an upward and downward motion relative to the target when activated, whereby the upward motion reduces the volume of the fluid dispenser chamber to provide a positive pressure in the fluid dispenser chamber relative to the pressure of the target whereby the positive pressure causes the fluid to be transported from the fluid dispenser chamber into the target.

Another embodiment of the present invention is a fluid transport apparatus for withdrawing target fluid from a target, and infusing storage fluid into the target the fluid transport apparatus comprising: at least one fluid collection chamber having a collection target wall and a collection distal wall opposite of the collection target wall, a collection side wall that connects the collection distal wall with the collection target wall, whereby the collection target wall is adapted for being mated against the target while the transport apparatus is in use; at least one fluid dispenser chamber having a storage target wall and a storage distal wall opposite of the storage target wall, a storage side wall that is proximate to or integral with the collection side wall so as to connect the storage distal wall with the storage target wall, thereby forming a generally common side wall defined by the side walls being adjacent or integral with one another, and whereby the storage target wall is adapted for being mated against the target while the transport apparatus is in use; an actuator means that is in mechanical communication with the common side wall, the actuator means reciprocates when activated; at least one cutting device attached to the target wall of each of the fluid collection chamber and fluid dispenser chamber and extending away from the respective chambers, each such cutting device having a passage for transporting fluid there through; and a power supply operatively connected to the actuator means for activating the actuator, the actuator means reciprocates in an upward and downward motion relative to the interior of the respective chambers when activated, whereby the upward motion contracts the volume of the fluid dispenser chamber to provide a positive pressure in the fluid dispenser chamber relative to the pressure of the target, whereby the positive pressure causes the fluid to be transported from the fluid dispenser chamber into the target, and whereby the upward motion expands the volume of the collection chamber to provide a negative pressure in the fluid collection chamber relative to the pressure of the target whereby the negative pressure causes the fluid to be transported from the target into the fluid collection chamber.

Further, an additional embodiment of the present invention is a fluid transport apparatus for withdrawing fluid from a target, whereby the target has target passages extending therein, the fluid transport apparatus comprising: at least one fluid collection chamber having a target wall and a distal wall opposite of the target wall, whereby the target wall is adapted for being mated against the target while the transport apparatus is in use; an actuator means that is in mechanical communication with the distal wall, the actuator means reciprocates when activated; at least one aperture disposed on the target wall of the fluid collection chamber so as to be aligned with the respective target passage when the target wall is mated against the target, thereby forming a passage between the target passage and the target wall aperture for transporting fluid there through; and a power supply operatively connected to the actuator means for activating the actuator, the actuator means reciprocates in an upward and downward motion relative to the target when activated, whereby the upward motion expands the volume of the collection chamber to provide a negative pressure in the fluid collection chamber relative to the pressure of the target whereby the negative pressure causes the fluid to be transported from the target into the fluid collection chamber.

Finally, another embodiment of the present invention is a method of transporting fluid from a target using a fluid transport apparatus, the method comprising the steps of: inserting at least one cutting device into the target wherein the cutting device comprises a passage for transporting fluid there through to a fluid collection chamber, the fluid collection chamber comprising a target wall that is adapted for being mated against the target while the transport apparatus is in use, the fluid collection chamber having a distal wall that is opposite the target wall; and applying a negative pressure in the fluid collection chamber, wherein the negative pressure causes the fluid to be transported or withdrawn from the target into the passages of the cutting devices and transported or withdrawn into the fluid collection chamber. Wherein the application of negative pressure comprises the following steps: expanding the volume of the fluid collecting chamber via a fluid valve means disposed on the target wall. Wherein the volume expansion of the fluid collection chamber comprises the following steps: activating an actuator means that is in mechanical or electrical communication with the distal wall; the actuator means reciprocates causing the distal wall to reciprocate in an upward and a downward motion relative to the target when activated, whereby the upward motion expands the volume of the fluid collection chamber to provide the negative pressure in the fluid collection chamber relative to the pressure of the target and whereby the negative pressure causes the fluid to be transported from the target into the fluid collection chamber.

These and other objects, along with advantages and features of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings in which:

FIG. 7(A) also shows the target wall apertures that are aligned with the target passages.

DETAILED DESCRIPTION OF THE INVENTION

Figure 1:
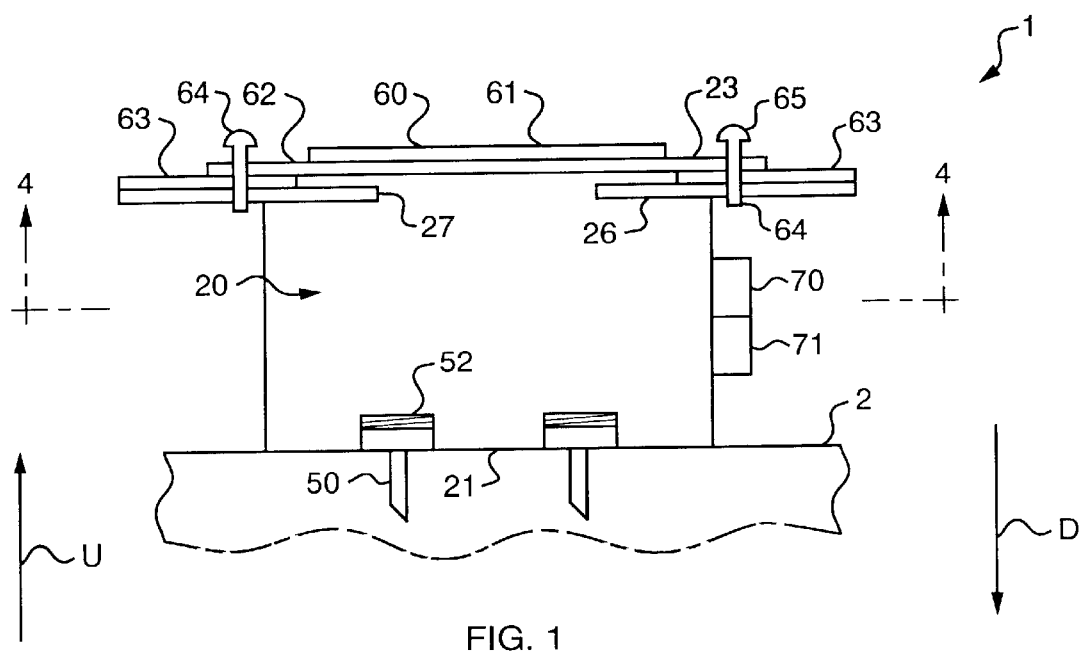
FIG. 1 shows a sectional view of the fluid transport apparatus having the actuator in the generally planar position.

Turning now to the drawings, FIGS. 1–5 show a fluid transport apparatus 1 for withdrawing fluid from a target 2 as part of the first preferred embodiment of the present invention. For discussion purposes, the fluid transport apparatus 1 will be described in the context of an apparatus and method capable of providing a percutaneous or direct removal of blood and other body fluids from the body or target 2, but is not limited thereto. The fluid transport apparatus 1 has a fluid collection chamber 20 that has attached thereto cutting devices 50. The cutting devices 50 are used to make incisions through the wall or skin of the body or target 2 by inserting the cutting device or devices 50 through the wall of the body for automatically removing blood or other tissue fluids from the skin or other tissues. In the preferred embodiment, the depth of penetration of the cutting devices 50 is about 0.5 mm to about 5 mm in depth, and could be greater in other tissue applications. Merely by way of example, the cutting devices 50 may be hypodermic needles, or equivalent known construction, having an inner diameter in the range of about 27 GA (204 µm) to about 18 GA (834 µm). Alternatively, the inner diameter may have a range of about 10 µm to about 1,000 µm. Also, the cutting device may be a tubular structure or the like.

Still referring to FIGS. 1–5, the first preferred embodiment of the present invention includes a fluid collection chamber 20 with an actuator means 60 that at least partially functions as the distal wall 23 opposite the target wall 21. The cutting devices 50 are attached to the target wall 21 so as to maintain a seal between the collection chamber 20 and the target 2. An effective seal of the transport apparatus 1 is imperative in maintaining the pressure gradient that is generated during fluid removal.

In the operating mode of the transport apparatus, the actuator means 60 is energized by a power supply means 70. In the preferred embodiment the actuator means 60 is a piezoelectric film 61. The piezoelectric film 61 is energized when a voltage from the power supply means 70 is applied across a conductive (or semi-conductive) contact 62 which is in electrical communication with the piezoelectric film 61. In the preferred embodiment, the piezoelectric film 61 is normally bent in its resting position, i.e., when it is inactivated in the power cycle.

One skilled in the art would appreciate variations pertaining to the piezoelectric film 61. The piezoelectric film 61 may have a stacking relation with multiple piezoelectric elements whereby the stack may be characterized having a "clam shell" stack or "potato chip" stack, both of which produce larger deflections or support larger pressures.

Next, as best shown in FIG. 1, as the voltage is applied across the conductive contact 62 and the piezoelectric film 61, the film 61 is activated, thereby changing the piezoelectric film to a generally flat or planar shape. It is contemplated that some types of film 61 will not completely straighten out A flexible seal 63 is disposed between the conductive contact 62 and a mounting surface 26 (or also may laterally separate the actuator (60, 61) from the mounting surface 26). For example, if the flexible seal 63 is disposed between the distal wall 23 and the mounting surface 26 then the flexible seal allows for the lateral movement and/or separation of the distal wall 23 as the distal wall reciprocates between positions. The flexible seal 63 maintains an airtight seal between the fluid collection chamber 20 and the distal wall 23. The airtight seal is maintained while the piezoelectric film 61 reciprocates from its bent position as disclosed in FIG. 2 to its generally straight position as disclosed in FIG. 1.

Figure 2:
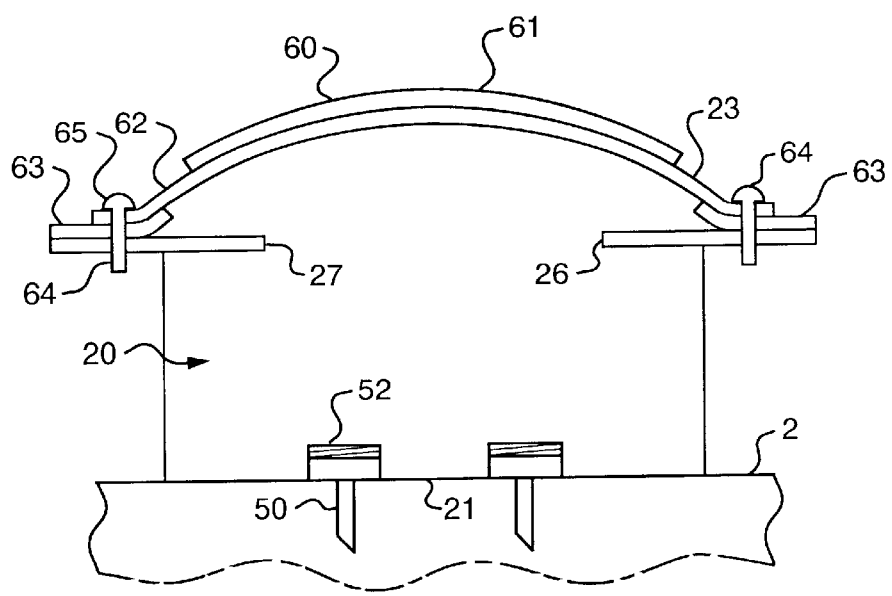
FIG. 2 shows a sectional view of the fluid transport apparatus having the actuator in the generally bent position.

In the operating mode, the actuator means 60 (or piezoelectric film 61 in the preferred embodiment) reciprocates between an upward bent position, as shown in FIG. 2, thereby defining a concave surface in relation to the fluid collection chamber 20 and a downward generally straight position, as shown in FIG. 1, thereby defining a generally planar surface.

Referring to FIGS. 1 and 2, a fluid valve means 52 is provided so as to prevent the fluid from leaking out of the collection chamber and back into the target 2. Various valve type mechanisms of known construction may be used such as small one-way valves or leaflets. As will be discussed later, the valve means 52 can be reversed so as to reverse flow direction.

Figure 3:
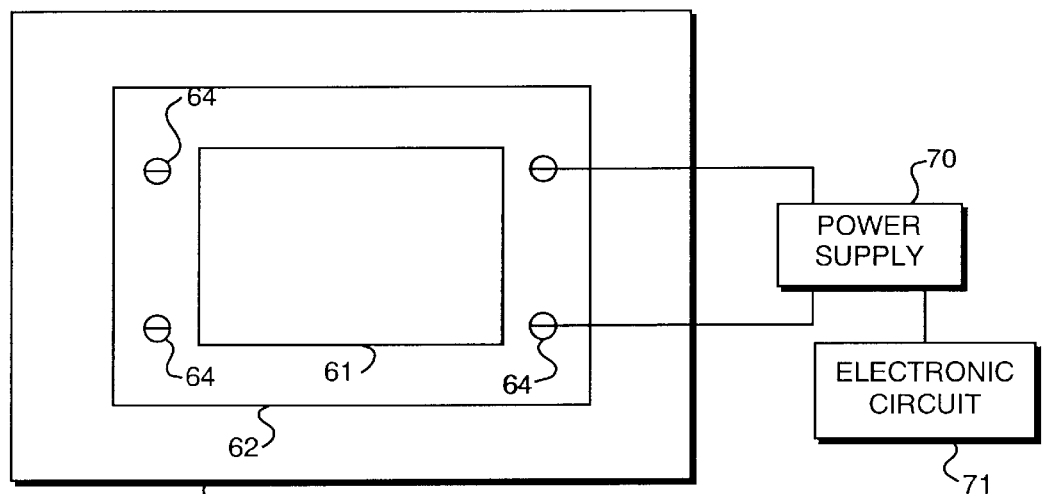
FIG. 3 shows a top plan view of the fluid transport apparatus 1 showing the actuator disposed on the conductive contact that is disposed on the flexible seal.
Figure 11:
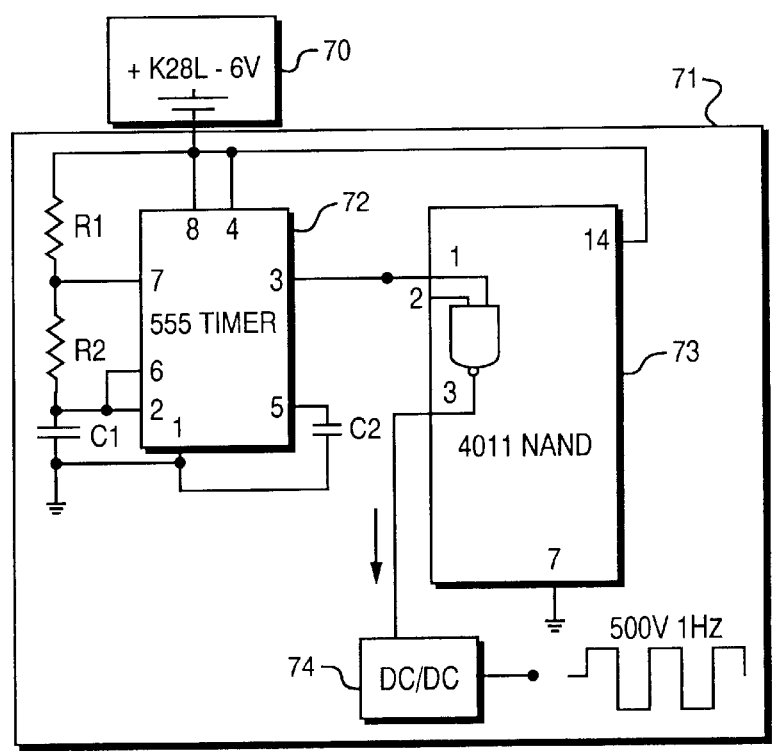
FIG. 11 shows an illustrative embodiment of the electronic circuit.

As best shown in FIGS. 3, 6, and 11, an electronic circuit 71 provides the timing logic to drive the piezoelectric film 61. This electronic circuit 71 or a comparable circuit can be miniaturized and housed as part of a disposable device (fluid transport apparatus 1). One skilled in the art would appreciate that various digital or analog circuits could be utilized, including select hardware, software or firmware. Referring specifically to FIG. 11, an illustrative design provides a flip-flop circuit utilizing a 555 timer chip 72 that drives the piezoelectric film. The 4011 NAND chip 73 is being used as a single ended voltage follower that will stabilize the output signal. One skilled in the art would recognize that various power supplies 70 could be used. For instance, the preferred embodiment of the present invention may utilize a Lithium/Manganese Dioxide battery for powering the circuit 71 whose output is a 5V square wave of 1 Hz. The output is fed into a DC/DC converter 74 to increase the voltage from 5 to 500V without the need for a heat sink.

It should be noted that in an alternative embodiment of the present invention, a heat sink is an additional element that may be used with a solenoid 90 as the actuator means 60. However, the use of a solenoid 90 would only require about 10V, therefore, the circuit 71 could be simplified to drive the solenoid 90. This electronic circuit 71 or a comparable circuit can be miniaturized and housed as part of a disposable device (fluid transport apparatus 1).

To that effect, referring briefly to FIG. 9 (as it will be discussed in greater detail infra), it is contemplated that an alternative embodiment includes a fluid transport apparatus 1 comprising detachable module units, whereby it provides an off board power supply 70 that will be used to generate the desired input voltage, along with an off board electronic circuit 71 and actuator means 60.

As best shown in FIGS. 1–4, displacement guides 64 provide a means of securing the conductive contact 62 to the fluid transport apparatus 1 at the mounting surface 26. The displacement guides 64, also provide a means for adjusting the range of movement by which the piezoelectric film 61 can reciprocate from the straight position (as shown in FIG. 1.) to the bent position (as shown in FIG. 2). Any apertures that the displacement guide 64 is disposed through may need to be elongated or slotted so as to allow for the lateral motion of the distal wall 23 and the related components while the distal wall 23 is reciprocating.

Alternatively, one skilled in the art would appreciate that the displacement guide 64 may be devices of various known construction such as clamps, screws, bolts, rods, tracks, couplings, latches, and pins.

The motion of the piezoelectric film 61 from the flat or planar position as shown in FIG. 1 to the displaced position as shown in FIG. 2 generates a negative pressure in the fluid collection chamber 20 that draws blood or fluid from the target 2 and into the collection chamber 20. It is contemplated that the rate of the displacement of the actuator 60 could be varied, with a nominal rate of 60 cycles per minute, and nominal vertical distance displacement of the actuator (distal wall) general centerpoint of about 0.5 cm to about 1.0 cm. Alternatively, the cycle rate may be effected at 30 cycles per minute or greater. Likewise, the distance displacement range could be provided at about 0.1 cm to 5.0 cm.

Next, FIG. 3 shows a top plan view of the fluid transport apparatus 1 showing the piezoelectric film 61 disposed on the conductive contact 62 that is disposed on the flexible seal 63. The top portions of the displacement guides 64 are also visible. Also shown in FIG. 3 is the power supply 70 and electronic circuit 71 in electrical communication with the conductive contact 62.

Figure 4:
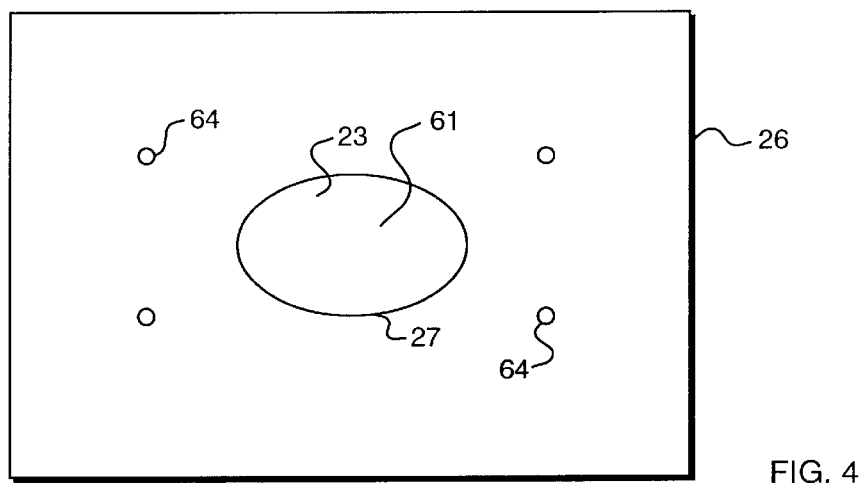
FIG. 4 shows the bottom of the mounting surface having an aperture.

FIG. 4 is a sectional view of the fluid transport apparatus 1 (looking in direction 4—4 of FIG. 1). FIG. 4 shows the bottom of the mounting surface 26 whereby the mounting surface 26 has an aperture 27. The aperture 27 allows the distal wall 23 or conductive contact 62 to be open to the fluid collection chamber 20 located below the mounting surface 26. One skilled in the art would appreciate that the mounting surface 26 could be various shapes so long as the distal wall 23 and the related elements can be mounted. For example, the mounting surface could coincide with the circumference of the fluid collection chamber 20, or an air storage chamber 41 (to be discussed later), and thus the surface aperture 27 would generally be defined by the circumference of the fluid collection chamber 20.

Figure 5:
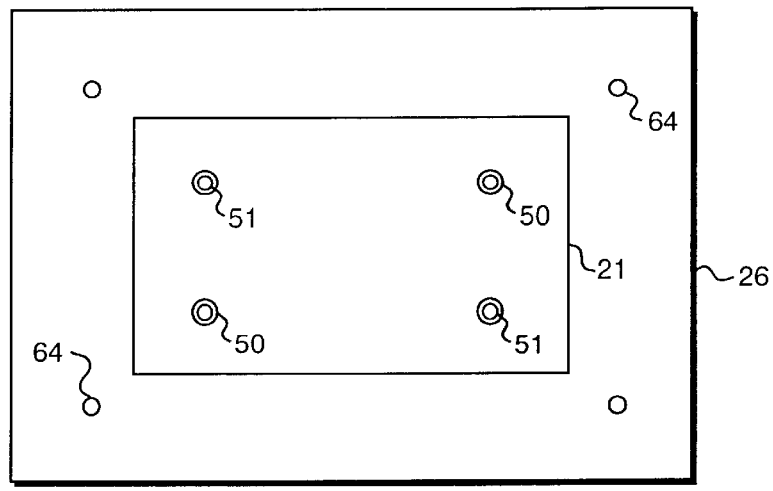
FIG. 5 shows a bottom plan view of the fluid transport apparatus showing a cross-sectional view of the cutting devices and their respective passage or bore.

FIG. 5 shows a bottom plan view of the fluid transport apparatus 1 showing a cross-sectional view of the cutting devices 50 and their respective passages 51 as the cutting devices 50 extend in a normal direction away from the target wall 21. Each passage 51 adapted for transporting fluid there through. It is contemplated that the passages can be bores, apertures, cavities, chamber ducts, openings, orifices, or slots. Also shown are cutting device restraints 54 that help retain the cutting devices 50 within the target wall 21 and/or a manifold 25 (discussed below). For example, the device restraints 54 may be collars, washers, weld spots, solder points, and the like.

Figure 10:
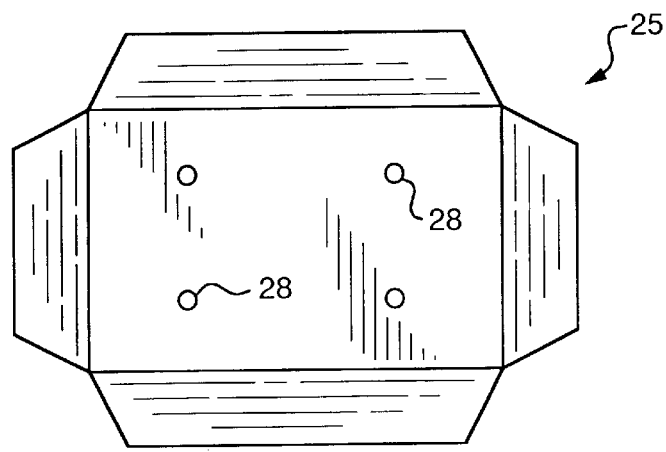
FIG. 10 shows a manifold having manifold apertures to accommodate the cutting devices.

As shown in FIG. 10, the target wall 21 may be comprised of a manifold 25 having manifold apertures 30 to accommodate the cutting devices 50 (or form the cutting devices 50). The manifold 25, having substantially flexible properties, enables the target wall 21 to effectively mate to the contours of the target 2. It should be understood that the manifold 25 may be integral with the target wall 21 or juxtaposed to the target 21.

Figure 6A:
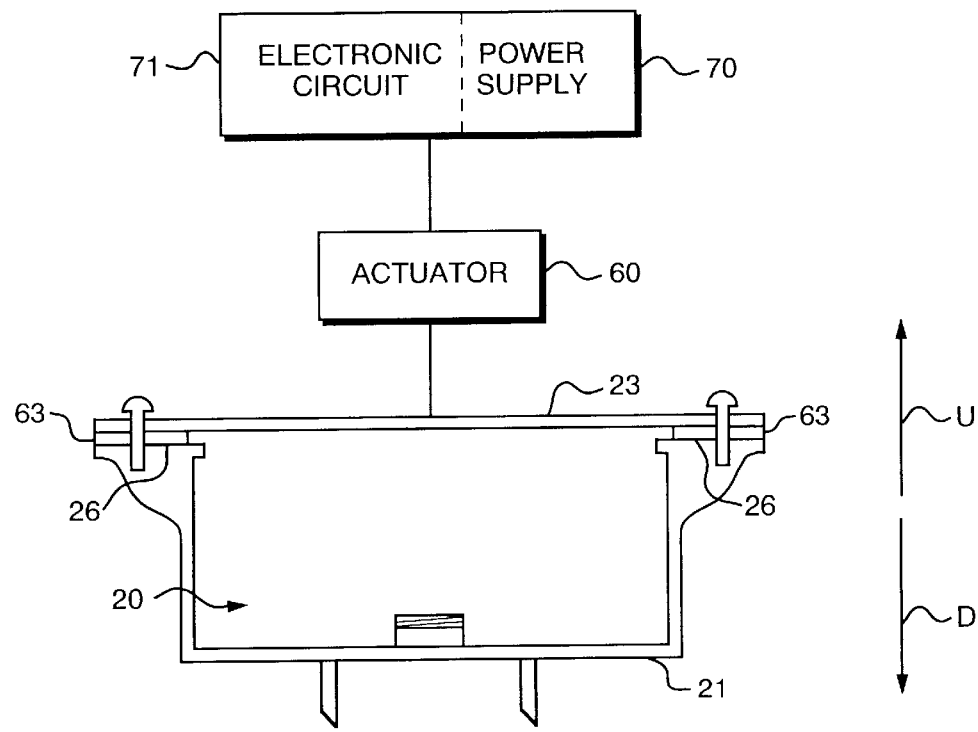
FIGS. 6(A) and 7(A) show a sectional view of the fluid transport apparatus wherein the actuator is in the generally planar position and generally bent position, respectively.
Figure 7A:
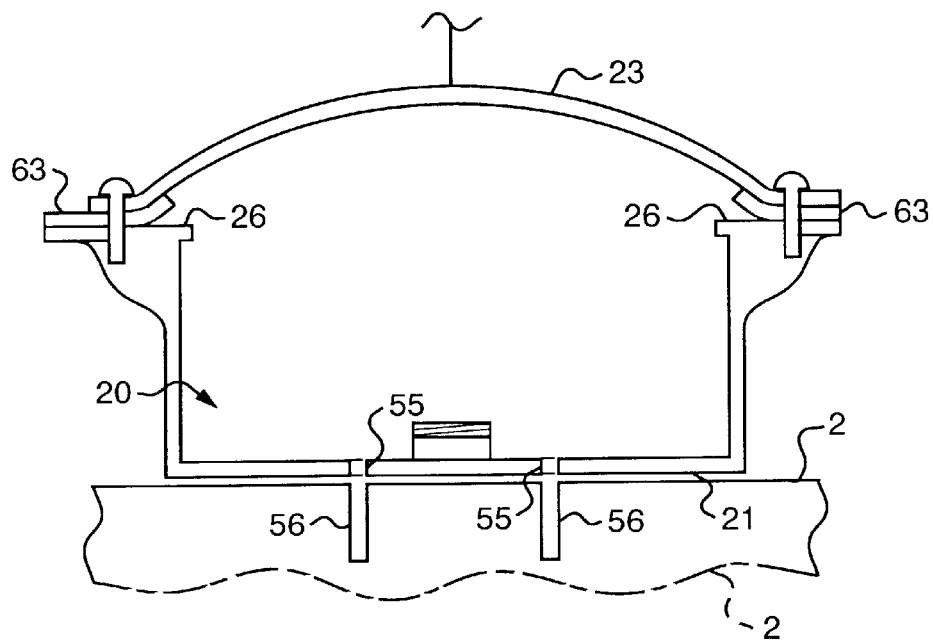

FIGS. 6(A) and 7(A) show the fluid transport apparatus 1 using a general actuator arrangement Whereby the actuator could be in addition to piezoelectric film, a solenoid, memory alloy, evacuated chamber, or spring loaded mechanism. The actuator 60 will reciprocate the distal wall 23 so as to move upward from its generally straight position (generally planar) as disclosed in FIG. 6(A) to the bent position(generally concave) as disclosed in FIG. 7(A).

Figure 6B:
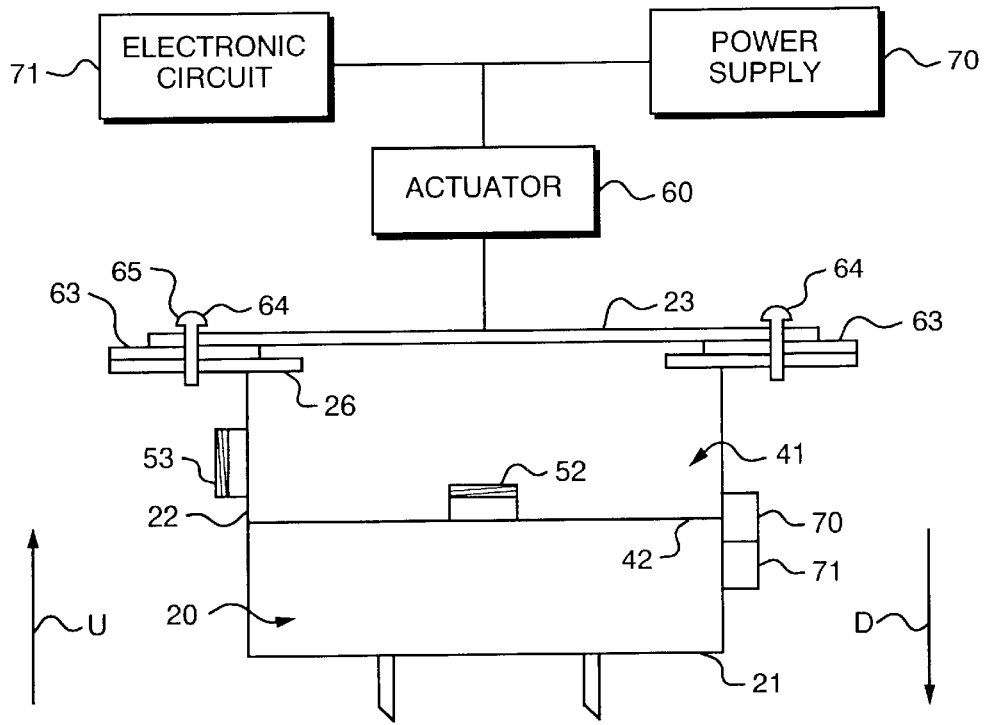
FIGS. 6(B) and 7(B) show a sectional view of the fluid transport apparatus including an air storage chamber wherein the actuator is in the generally planar position and generally bent position, respectively.
Figure 7B:
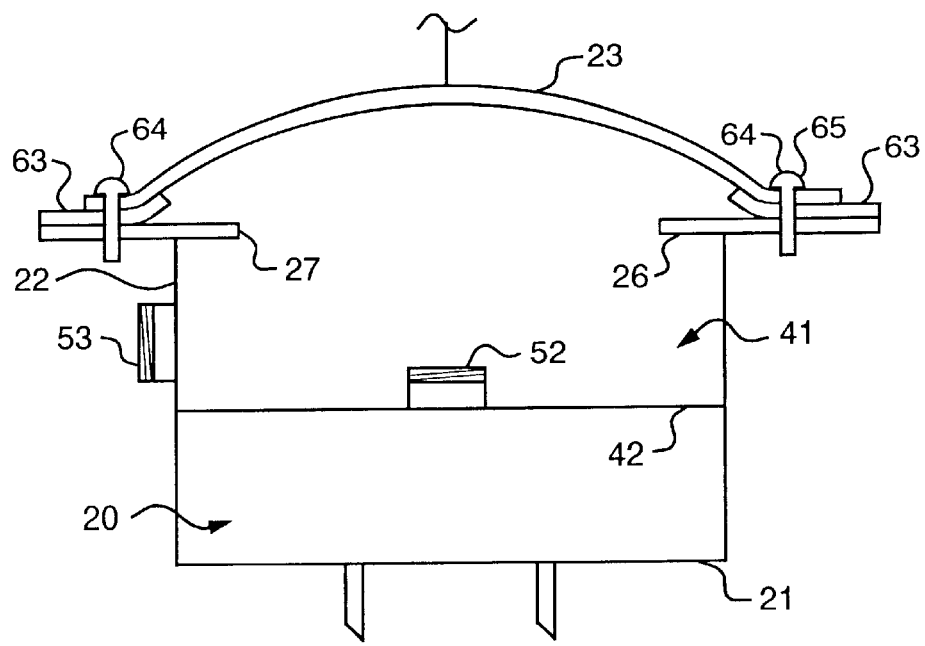

FIGS. 6(B) and 7(B) show a second and preferred embodiment of the fluid transport apparatus 1 of the present invention. The second preferred embodiment includes an air storage chamber 41 that is adjacent to the fluid collection chamber 20 and essentially shares a common intermediate wall 42. Also provided in the second embodiment is the fluid valve(s) 52 disposed in the intermediate wall 42. The fluid valve 52 allows air from the fluid collection chamber 20 to move into the air storage chamber 41, and also prevents any fluid that accumulates in the fluid collection chamber 20 from entering into the air storage chamber 41. Also, regarding an optional feature that may be added to the aforementioned second embodiment, an exhaust air valve 53 is disposed on a sidewall 32 of the air storage chamber 41. It should be understood that an exhaust valve 53 may be applied to the fluid collection chamber 20 of the first preferred embodiment.

Accordingly, as best shown in FIGS. 6(B) and 7(B), during the upward motion of the distal wall 23 the exhaust air valve 53 closes under the resultant negative pressure so as to prevent air from being released out from the air storage chamber 41; and during the downward motion of the distal wall 23 the exhaust air valve 53 opens to allow air to be released out of the air storage chamber 41.

Figure 8A:
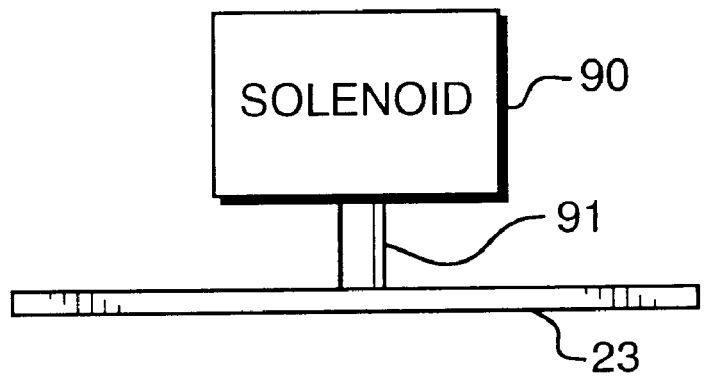
FIGS. 8(A) and 8(B) show a solenoid mechanism in relation to the distal wall and the general components of the solenoid mechanism.
Figure 8B:
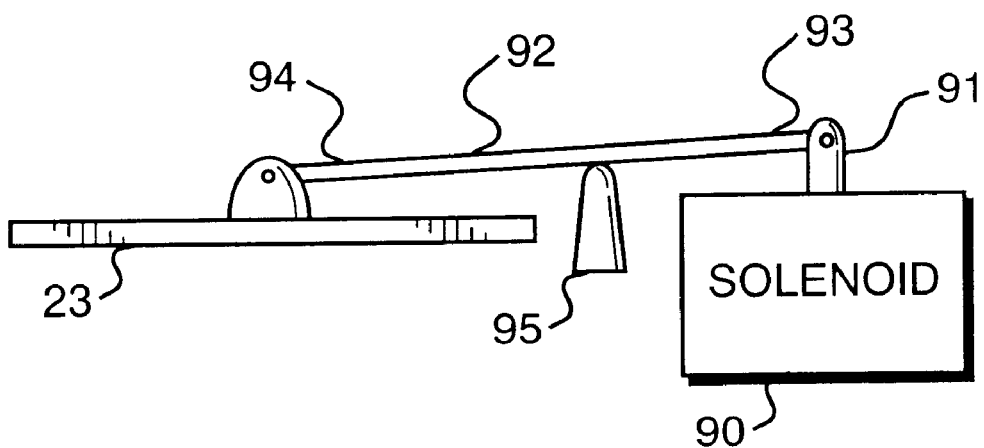

Moreover, the second preferred embodiment may include various forms of actuator devices 60, whereby the given actuator device 60 is in mechanical communication with the distal wall 23. As the actuator device 60 reciprocates, it causes the distal wall 23 to reciprocate in an upward and a downward motion relative to the target wall 21. As such, the upward motion expands the volume of the air storage chamber 41 to provide a negative pressure in the air storage chamber 41 and fluid collection chamber 20 relative to the pressure of the target 2. The negative pressure causes the fluid to be transported from the target 2 into the fluid collection chamber 20. Referring to FIGS. 8(A) and 8(B), the solenoid actuator device 90 has a piston 91 that reciprocates and is in mechanical communication with the distal wall 23. The reciprocation of the solenoid piston 91 causes the distal wall 23 to reciprocate between a bent position defining a concave surface in relation to the air storage chamber 41 to a straight position defining a generally planar surface.

As solenoids are known in the art there are various means available to attach the solenoid device 90 to the distal wall 23. Merely by way of example, FIG. 8(B) illustrates the details of construction whereby a lever arm 92 has one solenoid end 93 rotatably attached to the solenoid piston 91 and its other chamber end 94 rotatably attached to the distal wall 23. A fulcrum 95 is proximately located, strategically, to the lever arm 92 so that the lever arm 92 can pivot on the fulcrum 95 when the solenoid piston 91 reciprocates.

Figure 9A:
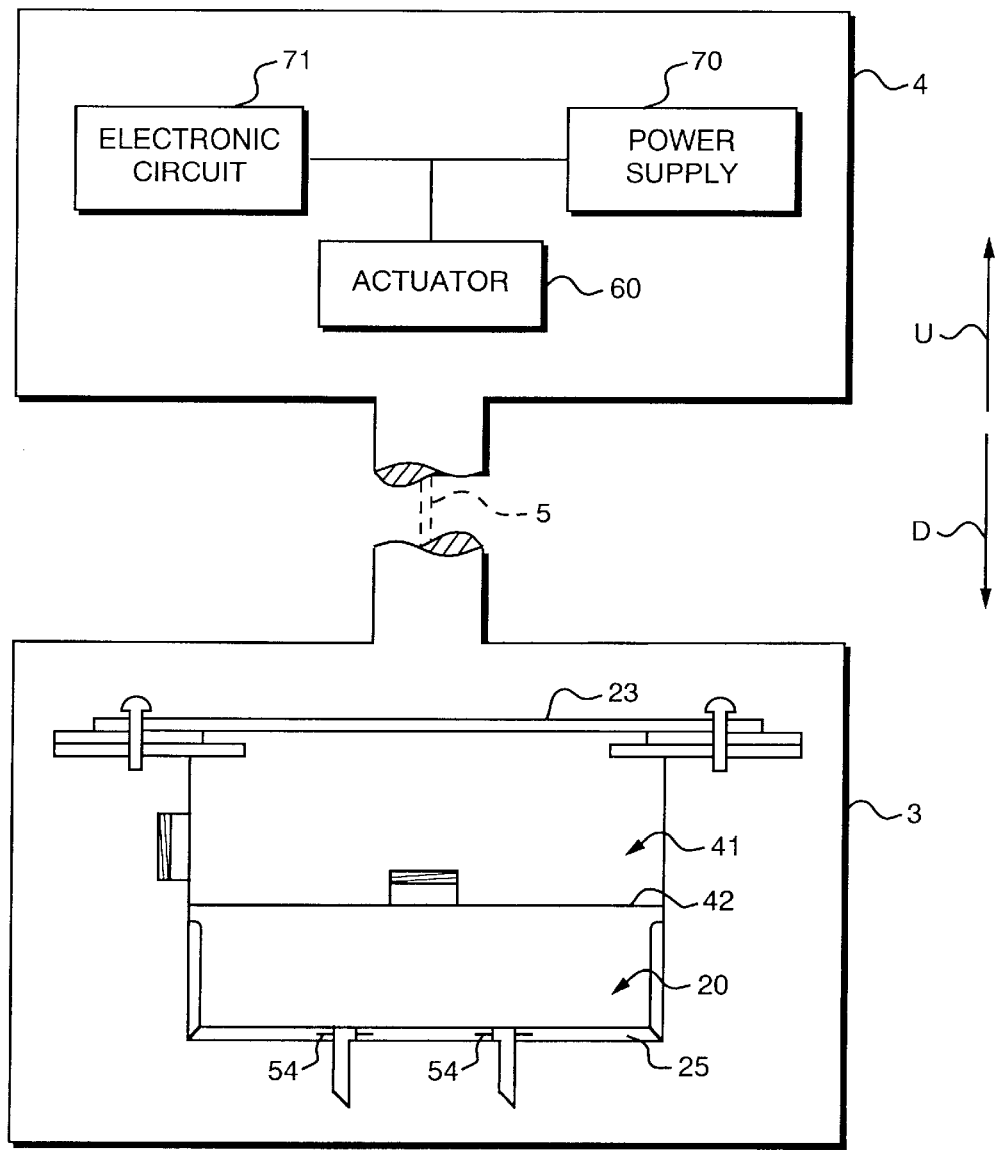
FIGS. 9(A) and 9(B) show the fluid transport apparatus comprising first and second detachable modules.

FIG. 9(A) shows a third and preferred embodiment of the fluid transport apparatus 1 of the present invention whereby the fluid transport apparatus 1 comprises a first and second detachable module. The detachable fluid transport apparatus 1 includes a latching mechanism 5 providing mechanical and/or electrical communication between the module sections 3, 4. The latching mechanism 5 serves as an attachment means and may constitute various embodiments including some of the following: latches, couplings, sockets, infrared (IR) communication, radio frequency (RF), Blue Tooth communication, electrical and mechanical connectors.

As shown in FIG. 9(A), the first detachable modular section 3 includes various elements including, but not limited thereto, the fluid collection chamber 20 and air storage chamber 41. Similarly, the second detachable section 4 includes various elements including, but not limited thereto, the actuator 60, power supply 70, and electronic circuit (timing circuit/chip) 71.

Figure 9B:
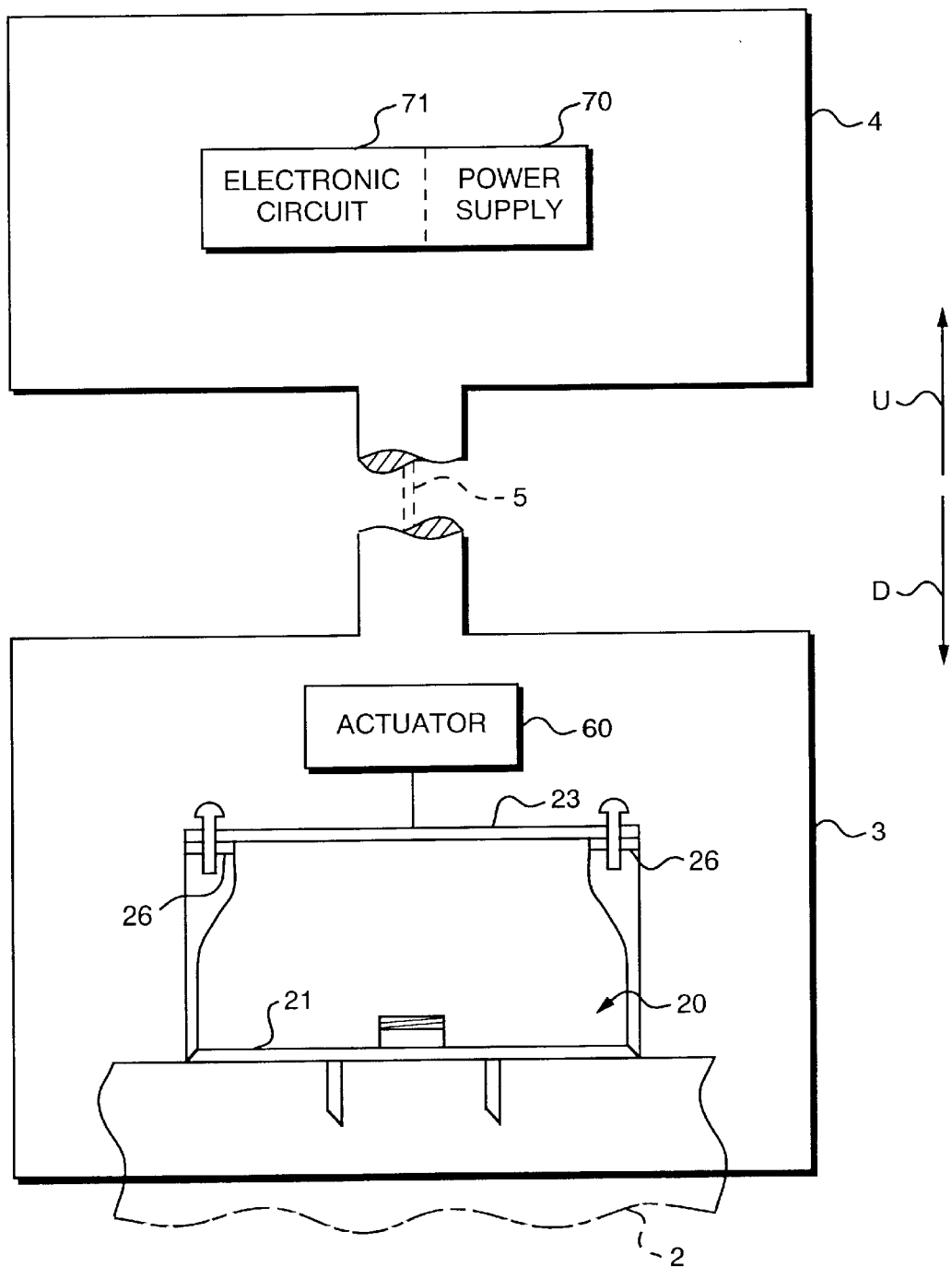

FIG. 9(B) shows a fourth and preferred embodiment of the fluid transport apparatus 1 of the present invention, similar to the previous embodiment, whereby the fluid transport apparatus 1 comprises a first and second detachable module. As shown in FIG. 9(B), the first detachable modular section 3 includes various elements including, but not limited thereto, the fluid collection chamber 20 and actuator 60. Similarly, the second detachable section 4 includes various elements including, but not limited thereto, the power supply 70, and electronic circuit (timing circuit/logic chip) 71.

Figure 13:
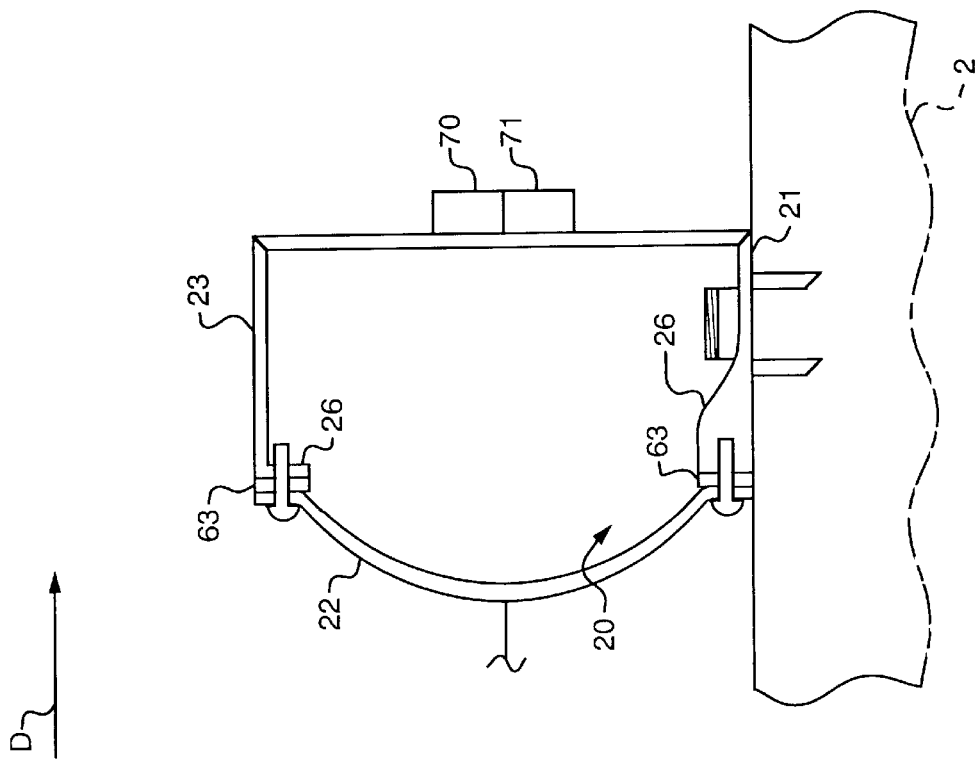
FIGS. 12 and 13 show an embodiment of the fluid transport apparatus whereby the actuator is mechanically connected to the side wall of the fluid collection chamber.
Figure 12:
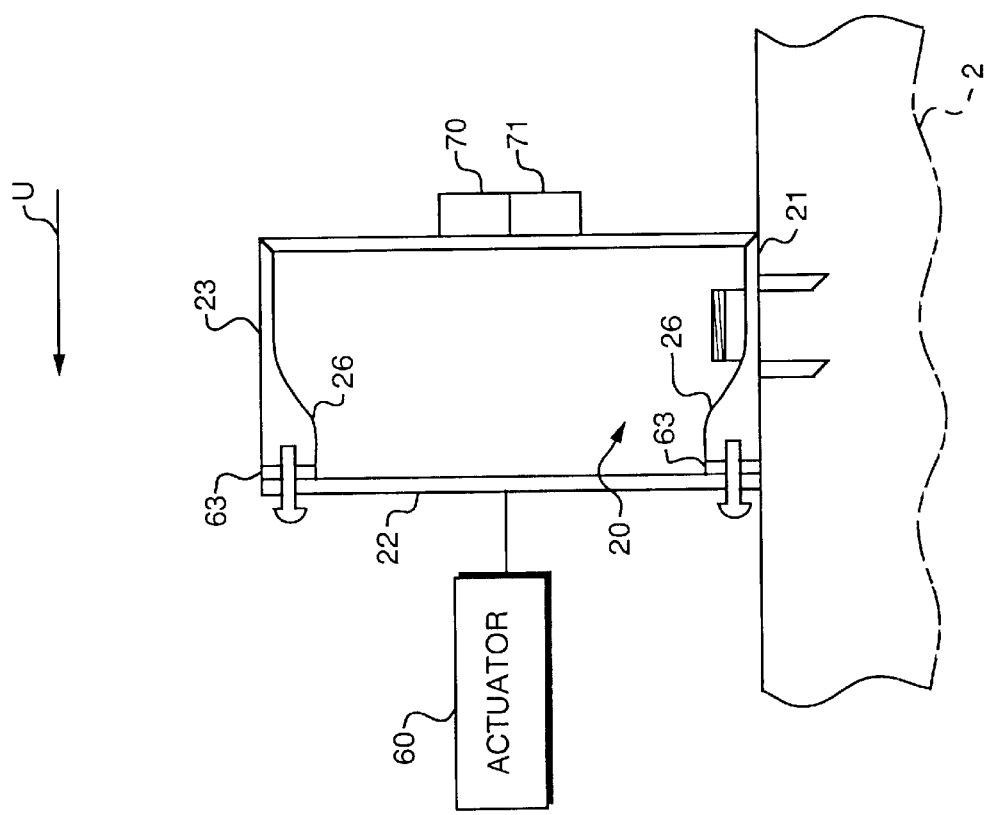

FIGS. 12 and 13 show a fifth and preferred embodiment of the present invention whereby the actuator 60 is mechanically connected to the side wall 22 of the fluid collection chamber 20. Whereby the actuator could be a piezoelectric film, a solenoid, memory alloy, spring loaded mechanism or the like. The actuator 60 will reciprocate the side wall 22 so as to move it upward starting from its generally straight position (generally planar) as disclosed in FIG. 12 to its bent position(generally concave) as disclosed in FIG. 13.

A sixth and preferred embodiment of the present invention could be applied to any of the aforesaid embodiments. That is, the fluid transport apparatus would be used for infusing fluids into the target, rather than withdrawing fluids. In particular, the fluid valves 52 are reversed so that as the actuator means reciprocates in an upward and downward motion relative to the interior of the fluid collection chamber 20, the motion reduces the volume of the collection chamber 20 to provide a positive pressure in the fluid collection chamber relative to the pressure of the target 2. This positive pressure causes the fluid to be transported from the apparatus 1 into the target 2. The fluid valves 52 are placed in the direction whereby the flow of fluid moves into the target and is prevented from exiting back into the apparatus 1. It is also contemplated that the actuator direction could be reversed.

Figure 15:
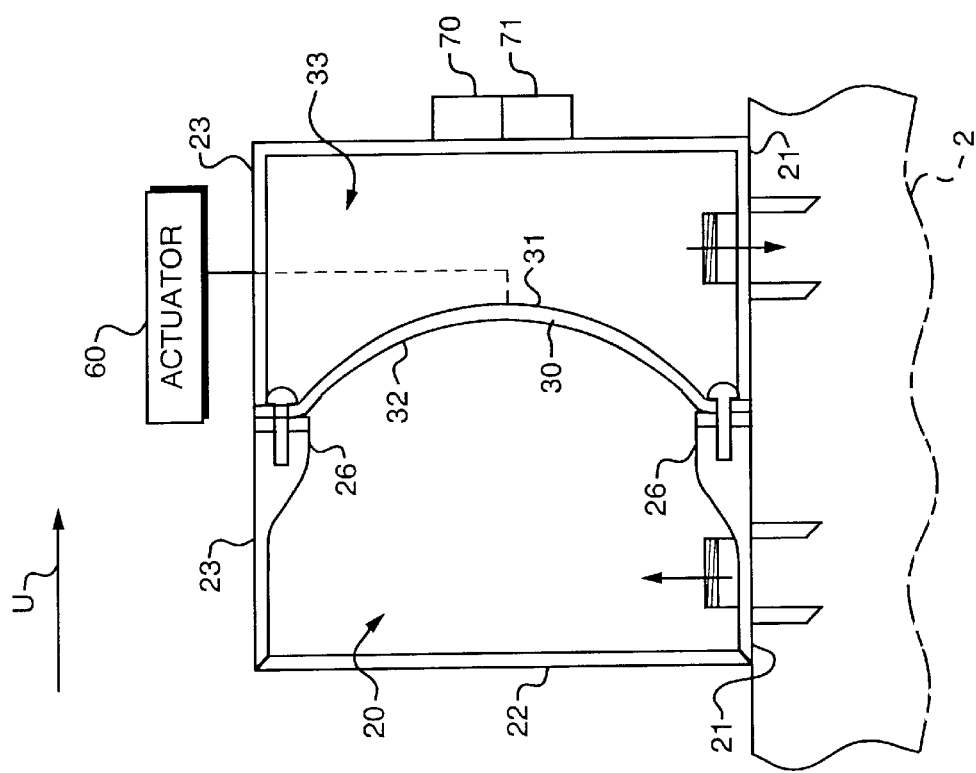
FIGS. 14 and 15 show an embodiment of the fluid transport apparatus whereby the fluid transport apparatus 1 is used to withdraw target fluid as well as to infuse dispenser fluid into the target.
Figure 14:
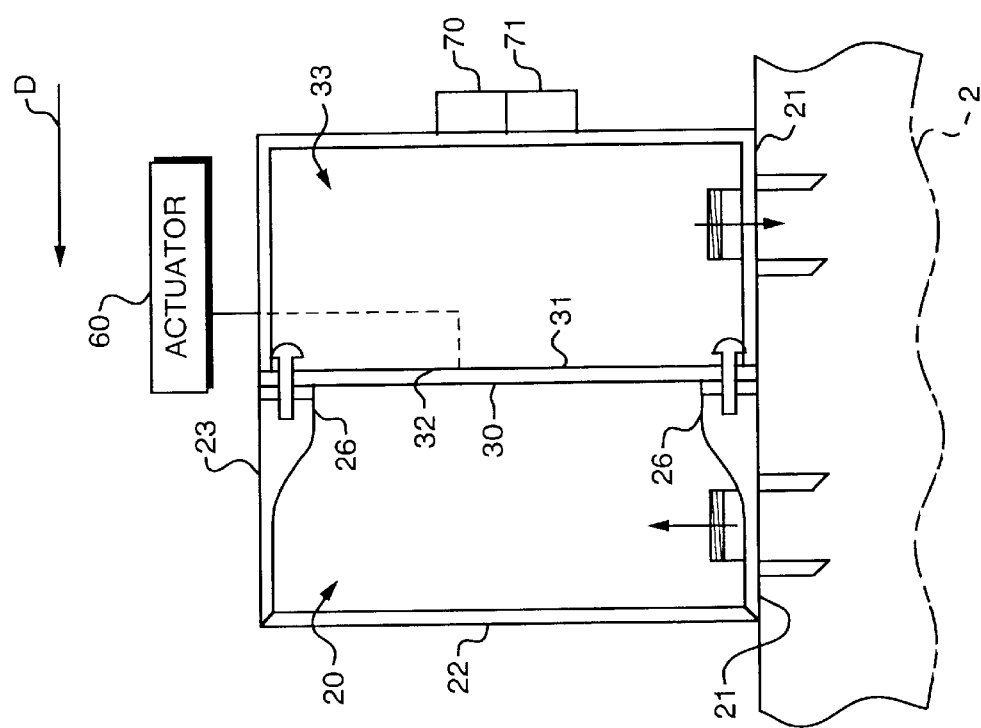

FIGS. 14 and 15 shows a seventh and preferred embodiment of the present invention whereby the fluid transport apparatus 1 is used to withdraw target fluid as well as to infuse dispenser fluid into the target. The apparatus 1 includes a fluid collection chamber 20 and an adjacent fluid dispenser chamber 33 sharing a common wall 32 with an actuator 60 connected thereto. In the operating mode, the actuator 60 reciprocates in an upward and downward motion relative to the interior of the respective chambers when activated. The upward motion contracts (reduces) the volume of said fluid dispenser chamber 33 to provide a positive pressure in the fluid dispenser chamber 33 relative to the pressure of the target 2 (FIG. 15). The positive pressure causes the fluid to be transported from the fluid dispenser chamber 33 into the target 2. Alternatively, the upward motion expands the volume of the collection chamber 20 to provide a negative pressure in the fluid collection chamber 20 relative to the pressure of the target 2 (FIG. 15). The negative pressure causes the fluid to be withdrawn from the target 2 into the fluid collection chamber 20.

FIG. 7(A) shows an eighth and preferred embodiment of the present invention whereby the fluid transport apparatus 1 is used on a target 2 that has target passages 56 formed therein. In particular, a surgical laser or other cutting device may be focused to a small beam width (around 0.5 to 2 mm in diameter) or device width and used to produce one or many target passages 56 in the target 2 tissue. The transport apparatus 1 (without the cutting devices 50 of the other embodiments) may then be attached as usual by aligning the target wall apertures 55 with the target passages 56 and used to transport blood/fluid into or out of the target 2 tissue.

The aforementioned embodiments will operate having various transport rates, as well as various number of cutting devices 50. For example, the transport rate of the fluid from the target 2 into the fluid collection chamber 20 is in the range of about 10 micro liters/minute to about 100 micro liters/minute, using about 1 to 10 cutting devices 50. Also, the apparatus 1 may be configured, for example, to run up to 1,000 micro liters/minute using about 1 to 500 cutting devices 50.

It should be noted that the pressure exerted for withdrawing bodily fluids needs to be reasonable so as to avoid any vessel or tissue structures from collapsing. An example of a reasonable negative pressure range which would not cause harm to the body is about 1–40 mmHg. Moreover, an achievable flow rate or transport rate of about 10 micro liter/min or greater is required in order to restore the tissues' normal function, reduce fluid accumulation, reduce tissue pressure, and/or distribute blood flow. This achievable flow rate (about 10 micro liter/min or greater) is greater than flow rates achievable with silicon-based Microsystems that are intended mainly for obtaining very small blood or fluid samples or infusing very small volumes of drugs.

Variations on the embodiments described above are possible. For example, the embodiments may use an actuator 60 that utilizes shape memory alloys in the membrane that could recoil when heated and generate a constant negative pressure.

Another variation is to apply an adhesive (skin seal) to the target wall so as to help hold the apparatus in place against the target.

Still yet, another variation on the embodiments is to incorporate a cotton-like wick or synthetic fiber wick or sponge to aid the fluid removal by capillary action. For example, the wick could be placed in the fluid collection chamber proximately to the cutting device passages to help carry the fluid away.

Moreover, another variation of the embodiments is that the apparatus could be used together with systemic intravenous administration of anticoagulants to provide a "tissue drainage" or "swelling prevention" system. In addition, attachment to the skin or tissue may also be achieved by a bandage external to the device or using adhesives or through flexible couplings to another structure that is not attached to the skin.

Finally, another variation of the embodiments is to incorporate alternating cycles of pressure and suction with oscillating diaphragm (i.e., injection/aspiration cycle). Further, the apparatus could incorporate a bioactive mixture administered via needles not subject to pressure (i.e., anticoagulant, antiseptic, anesthetic, and vasodilator fluids).

The embodiments described above provide a number of significant advantages. For instance, by removing the fluid, an advantage of the present invention is that the transport apparatus 1 restores the tissue's normal function by reducing fluid accumulation, restoring blood flow, and allowing time for growth of new vessels in tissues with obstructed blood vessels. It is envisioned that one primary application of the present invention will be the restoration of flow and reduction in tissue pressure in skin flaps and transplanted skin grafts, thereby improving chances of tissue survival.

A further advantage of the present invention is that the mechanical leech or transport apparatus would be useful in plastic and reconstructive surgery when venous congestion becomes, or is anticipated as, a problem. The prophylactic use of actual leeches is not currently done, so many flaps become severely congested before even receiving treatment. The present invention apparatus can be applied prophylactically before severe congestion occurs.

The present invention apparatus is a disposable, lightweight, electromechanical device capable of percutaneous or direct removal of blood and other body fluids, thereby replacing the need for a medicinal leech or large excisional skin wounds.

Another advantage of the present invention is that the mechanical leech or transport apparatus is readily available for use, with no need for special refrigerated storage in water or special handling precautions due to biohazards in the leech itself or in the biological fluid being transported from the patient.

In yet another advantage of the present invention transport apparatus is that it is self-contained (ideally in a small "Band-Aid" style bandage) and disposable, with a power supply and lightweight actuator within the device to create the negative pressure. For illustration purposes, the present invention can be entirely contained within a single unit having a size ranging from about 1 to 7 cm (length) by about 0.25 to 5 cm (height) by about 1 to 5 cm (width).

Another advantage of the present invention apparatus is that it is simple to use (not requiring trained personnel). It may be configured to avoid creating a large skin wound. Further, the apparatus avoids onerous setup procedures by medical personnel. The apparatus preferably is capable of creating multiple outlet sites of small size (number of outlets could range from 1 to a couple hundred). The multiple outlet sites serve to distribute blood flow to the skin region more uniformly and allow tissue pressure to be reduced.

A final advantage of the present invention is that the apparatus is also potentially useful in other applications, such as removal of tissue fluids in edematous (swollen) limbs after removal of lymphatic vessels or nodes in cancer patients or infusion of therapeutic agents. Moreover, the present invention would be useful for non-biological applications such as commercial or industrial fluid systems.

Thus, among other things, the fluid transfer apparatus of the present invention offers speed of application, reproducible fluid drainage, and greatly increased safety, along with ease of cleanup and disposal procedures. The present invention mechanical leeching is successful because it at least incorporates the positive aspects of medicinal leech therapy, eliminates the negative aspects of medicinal leech therapy, and maintains minimal invasiveness with controlled and contained bleeding.

What is claimed is:

1. A fluid transport apparatus for withdrawing fluid from a target, said fluid transport apparatus comprising:
    at least one fluid collection chamber having a target wall and a distal wall opposite of said target wall, whereby said target wall is adapted for being mated against the target while said transport apparatus is in use;
    an actuator means that at least partially forms a portion of said distal wall, said actuator means reciprocates when activated;
    at least one cutting device attached to said target wall of said fluid collection chamber and extending away from said fluid collection chamber, each such cutting device having at least one passage for transporting fluid there through; and
    a power supply operatively connected to said actuator means for activating said actuator, said actuator means reciprocates in an upward and downward motion relative to the target when activated, whereby the upward motion expands the volume of said collection chamber to provide a negative pressure in said fluid collection chamber relative to the pressure of said target whereby the negative pressure causes the fluid to be transported from the target into said fluid collection chamber.

2. The apparatus of claim 1, further comprising:
    a fluid valve means for each of said respective cutting devices disposed at the attachment end of said cutting devices, said fluid valve means allows the flow of fluid into said fluid collection chamber and prevents the fluid from exiting back into the target.

3. The apparatus of claim 2, whereby during the upward motion of said actuator means the fluid is pulled into said fluid collection chamber under the resultant negative pressure and during the downward motion of said actuator means chamber said valve means are closed to prevent the fluid from exiting from said collection chamber and back into the target.

4. The apparatus of claim 3, wherein said actuator means comprises:
    a piezoelectric film, whereby when said piezoelectric film is activated said film reciprocates between a bent position defining a concave surface in relation to said fluid collection chamber and a straight position defining a generally more planar surface.

5. The apparatus of claim 4, wherein said distal wall further comprises a conductive contact disposed on said piezoelectric film on the side of said piezoelectric film nearest to said target wall, said conductive contact being in electrical communication with said piezoelectric film.

6. The apparatus of claim 5, further comprising:
    a mounting surface disposed on said conductive contact on the side of said conductive contact nearest to said target wall, said mounting surface having an aperture to allow said distal wall to be open to said fluid collection chamber.

7. The apparatus of claim 6, further comprising:
    a flexible seal that is attached to, and disposed there between, said conductive contact and said mounting surface so as to provide an airtight seal between said collection chamber and said conductive contact.

8. The apparatus of claim 7, further comprising:
    a displacement means for allowing said distal wall to move upward to a first predetermined position and downward to a second predetermined position as said piezoelectric film is reciprocating.

9. The apparatus of claim 8, wherein said displacement means comprises:
    at least one elongated displacement guide, wherein said displacement guide is disposed through said conductive contact and has one of its ends affixed to said mounting surface, said displacement guide having a longitudinal axis that is generally parallel to the upward and downward reciprocating movement of said piezoelectric film, and said displacement guide further including a distal end that is opposite said fixed end and that extends upward so as to allow said distal wall to move upward to the first predetermined position.

10. The apparatus of claim 1, wherein said target wall comprises:
    a flexible manifold for mating to the contours of the target.

11. The apparatus of claim 1, whereby the transport rate of the fluid from the target into said fluid collection chamber is in the range of about 10 micro liters/minute to about 100 micro liters/minute.

12. The apparatus of claim 11, whereby the number of said cutting devices that the apparatus comprises is about 1 to about 10.

13. The apparatus of claim 1, whereby the transport rate of the fluid from the target into said fluid collection chamber is in the range of about 1 micro liters/minute to about 1000 micro liters/minute.

14. The apparatus of claim 13, whereby the number of said cutting devices that the apparatus comprises is about 1 to about 500.

15. A fluid transport apparatus for withdrawing fluid from a target, said fluid transport apparatus comprising:
at least one fluid collection chamber having a target wall and a distal wall opposite of said target wall, whereby said target wall is adapted for being mated against the target while said transport apparatus is in use;
an actuator means that is in mechanical communication with said distal wall, said actuator means reciprocates when activated;
at least one cutting device attached to said target wall of said fluid collection chamber and extending away from said fluid collection chamber, each such cutting device having a passage for transporting fluid there through; and
a power supply operatively connected to said actuator means for activating said actuator, said actuator means reciprocates in an upward and downward motion relative to the target when activated, whereby the upward motion expands the volume of said collection chamber to provide a negative pressure in said fluid collection chamber relative to the pressure of said target whereby the negative pressure causes the fluid to be transported from the target into said fluid collection chamber.

16. The apparatus of claim 15, further comprising:
a fluid valve means for each of said respective cutting devices disposed at the attachment end of said cutting devices, said fluid valve means allows the flow of fluid into said fluid collection chamber and prevents the fluid from exiting back into the target.

17. The apparatus of claim 16, whereby during the upward motion of said actuator means the fluid is pulled into said fluid collection chamber under the resultant negative pressure and during the downward motion of said actuator means said valve means are closed to prevent the fluid from exiting from said collection chamber and back into the target.

18. The apparatus of claim 17, wherein said actuator means comprises:
a piezoelectric film, whereby when said piezoelectric film is activated said film reciprocates between a bent position defining a concave surface in relation to said fluid collection chamber and a straight position defining a generally more planar surface.

19. The apparatus of claim 17, wherein said actuator means comprises:
a solenoid device, whereby when said solenoid device is activated said solenoid has a piston that reciprocates; and
said piston is mechanically attached to said distal wall whereby when said solenoid piston reciprocates said distal wall reciprocates between a bent position defining a concave surface in relation to said air storage chamber to a straight position defining a generally planar surface.

20. A fluid transport apparatus for withdrawing fluid from a target, said fluid transport apparatus comprising:
at least one air storage chamber having an intermediate wall and a distal wall opposite of said intermediate wall;
at least one fluid collection chamber having a wall that is defined by said intermediate wall, said collection chamber further including a target wall opposite of said intermediate wall, whereby said target wall is adapted for being mated against the target while said transport apparatus is in use;
an actuator means that is in mechanical communication with said distal wall, said actuator means reciprocates when activated;
at least one cutting device attached to said target wall of said fluid collection chamber and extending away from said fluid collection chamber, each such cutting device having a passage for transporting fluid there through; and
a power supply operatively connected to said actuator means for activating said actuator means, said actuator means reciprocates causing said distal wall to reciprocate in an upward and a downward motion relative to the target when activated, whereby the upward motion expands the volume of said air storage chamber to provide a negative pressure in said air storage chamber and fluid collection chamber relative to the pressure of said target and whereby the negative pressure causes the fluid to be transported from the target into said fluid collection chamber.

21. The apparatus of claim 20, further comprising:
at least one fluid valve means disposed in said intermediate wall, said fluid valve means allows air from said fluid collection chamber to move into said air storage chamber and prevents any fluid that accumulates in said fluid collection chamber from entering into said air storage chamber.

22. The apparatus of claim 21, whereby during the upward motion of said distal wall the fluid is pulled into said fluid collection chamber under the resultant negative pressure and during the downward motion of said distal wall said valve means are closed to prevent the fluid in said fluid collection chamber from entering into said air storage chamber.

23. The apparatus of claim 22, further comprising:
a mounting surface disposed on said distal wall on the side of said distal wall nearest to said fluid collection chamber, said mounting surface having an aperture to allow said distal wall to be open with said air storage chamber.

24. The apparatus of claim 23, further comprising:
a flexible seal that is attached to, and disposed there between, said distal wall and said mounting surface so as to provide an airtight seal between said air storage chamber and said distal wall.

25. The apparatus of claim 24, further comprising:
a displacement means for allowing said distal wall to move upward to a first predetermined position and downward to a second predetermined position as said actuator means is reciprocating.

26. The apparatus of claim 25, wherein said displacement means comprises:
at least one elongated displacement guide, wherein said displacement guide is disposed through said distal wall and has one of its ends affixed to said mounting surface, said displacement guide having a longitudinal axis that is generally parallel to the upward and downward reciprocating movement of said distal wall, and said displacement guide further including a distal end that is opposite said fixed end and that extends upward so as to allow said distal wall to move upward to the first predetermined position.

27. The apparatus of claim 24, wherein said actuator means comprises:

a solenoid device, whereby when said solenoid device is activated said solenoid has a piston that reciprocates; and said piston is mechanically attached to said distal wall whereby when said solenoid piston reciprocates'said distal wall reciprocates between a bent position defining a concave surface in relation to said air storage chamber to a straight position defining a generally planar surface.

28. The apparatus of claim 27, further comprising:

a lever arm that is rotatably attached, at its solenoid end of said lever, to said solenoid piston;

said lever arm also being rotatably attached, at its air storage chamber end of said lever, to said distal wall; and a fulcrum proximately located to said lever so that said lever can pivot on said fulcrum when said solenoid piston reciprocates, whereby when said solenoid is activated said lever pivots and said distal wall reciprocates between a bent position defining a concave surface in relation to said air storage chamber to a straight position defining a generally more planar surface.

29. The apparatus of claim 22, further comprising:

an exhaust valve means disposed on said air storage chamber, whereby during the upward motion of said distal wall said exhaust valve means closes under the resultant negative pressure so as to prevent air from being released out from said air storage chamber, and during the downward motion of said distal wall said exhaust valve means opens to allow air to be released out of said air storage chamber.

30. The apparatus of claim 22, wherein said actuator means comprises:

a piezoelectric film, whereby when said piezoelectric film is activated said film reciprocates between a bent position defining a concave surface in relation to said fluid collection chamber and a straight position defining a generally more planar surface.

31. The apparatus of claim 20, wherein said target wall comprises:

a flexible manifold for mating to the contours of the target.

32. The apparatus of claim 20, whereby the transport rate of the fluid from the target into said fluid collection chamber is in the range of about 10 micro liters/minute to about 100 micro liters/minute.

33. The apparatus of claim 32, whereby the number of said cutting devices that the apparatus comprises is about 1 to about 10.

34. The apparatus of claim 20, whereby the transport rate of the fluid from the target into said fluid collection chamber is in the range of about 1 micro liters/minute to about 1000 micro liters/minute.

35. The apparatus of claim 34, whereby the number of said cutting devices that the apparatus comprises is about 1 to about 500.

36. A detachable fluid transport apparatus for withdrawing fluid from a target, said detachable fluid transport apparatus comprising a first section that is in communication with and detachable from a second section, said apparatus comprising:

an attachment means that fastens said first and second sections so as to be in communication with one another and to be detachable from one another, wherein said first section comprises:

at least one fluid collection chamber having a target wall and a distal wall opposite of said target wall, whereby said target wall is adapted for being mated against the target while said transport apparatus is in use; and at least one cutting device attached to said target wall of said fluid collection chamber and extending away from said fluid collection chamber, each such cutting device having a passage for transporting fluid there through, wherein said second section comprises:

an actuator means that is in mechanical communication with said distal wall; and a power supply operatively connected to said actuator means for activating said actuator means, said actuator means reciprocates causing said distal wall to reciprocate in an upward and a downward motion relative to the target when activated, whereby the upward motion expands the volume of said air storage chamber to provide a negative pressure in said air storage chamber and fluid collection chamber relative to the pressure of said target and whereby the negative pressure causes the fluid to be transported from said target into said fluid collection chamber.

37. A detachable fluid transport apparatus for withdrawing fluid from a target, said detachable fluid transport apparatus comprising a first section that is in communication with and detachable from a second section, said apparatus comprising:

an attachment means that fastens said first and second sections so as to be in communication with one another and to be detachable from one another, wherein said first section comprises:

at least one fluid collection chamber having a target wall and a distal wall opposite of said target wall, whereby said target wall is adapted for being mated against the target while said transport apparatus is in use;

at least one cutting device attached to said target wall of said fluid collection chamber and extending away from said fluid collection chamber, each such cutting device having a passage for transporting fluid there through; and an actuator means that is in mechanical communication with said distal wall, wherein said second section comprises:

a power supply operatively connected to said actuator means for activating said actuator means, said actuator means reciprocates causing said distal wall to reciprocate in an upward and a downward motion relative to the target when activated, whereby the upward-motion expands the volume of said air storage chamber to provide a negative pressure in said air storage chamber and fluid collection chamber relative to the pressure of said target and whereby the negative pressure causes the fluid to be transported from said target into said fluid collection chamber.

38. A detachable fluid transport apparatus for withdrawing fluid from a target, said detachable fluid transport apparatus comprising a first section that is in communication with and detachable from a second section, said apparatus comprising:

an attachment means that fastens said first and second sections so as to be in communication with one another and to be detachable from one another, wherein said first section comprises:

at least one air storage chamber having an intermediate wall and a distal wall opposite of said intermediate wall;

at least one fluid collection chamber having a wall that is defined by said intermediate wall, said collection chamber further including a target wall opposite of said intermediate wall, whereby said target wall is adapted for being mated against the target while said transport apparatus is in use; and at least one cutting device attached to said target wall of said fluid collection chamber and extending away from said fluid collection chamber, each such cutting device having a passage for transporting fluid there through, wherein said second section comprises:

an actuator means that is in mechanical communication with said distal wall; and a power supply operatively connected to said actuator means for activating said actuator means, said actuator means reciprocates causing said distal wall to reciprocate in an upward and a downward motion relative to the target when activated, whereby the upward motion expands the volume of said air storage chamber to provide a negative pressure in said air storage chamber and fluid collection chamber relative to the pressure of said target and whereby the negative pressure causes the fluid to be transported from said target into said fluid collection chamber.

39. A detachable fluid transport apparatus for withdrawing fluid from a target, said detachable fluid transport apparatus comprising a first section that is in communication with and detachable from a second section, said apparatus comprising:

an attachment means that fastens said first and second sections so as to be in communication with one another and to be detachable from one another, wherein said first section comprises:

at least one air storage chamber having an intermediate wall and a distal wall opposite of said intermediate wall;

at least one fluid collection chamber having a wall that is defined by said intermediate wall, said collection chamber further including a target wall opposite of said intermediate wall, whereby said target wall is adapted for being mated against the target while said transport apparatus is in use;

at least one cutting device attached to said target wall of said fluid collection chamber and extending away from said fluid collection chamber, each such cutting device having a passage for transporting fluid there through; and an actuator means that is in mechanical communication with said distal wall, wherein said second section comprises:

a power supply operatively connected to said actuator means for activating said actuator means, said actuator means reciprocates causing said distal wall to reciprocate in an upward and a downward motion relative to the target when activated, whereby the upward motion expands the volume of said air storage chamber to, provide a negative pressure in said air storage chamber and fluid collection chamber relative to the pressure of said target and whereby the negative pressure causes the fluid to be transported from said target into said fluid collection chamber.

40. A fluid transport apparatus for withdrawing fluid from a target, said fluid transport apparatus comprising:

at least one fluid collection chamber having a target wall and a distal wall opposite of said target wall, a side wall that connects said distal wall with said target wall, whereby said target wall is adapted for being mated against the target while said transport apparatus is in use;

an actuator means that is in mechanical communication with said side wall, said actuator means reciprocates when activated;

at least one cutting device attached to said target wall of said fluid collection chamber and extending away from said fluid collection chamber, each such cutting device having a passage for transporting fluid there through; and a power supply operatively connected to said actuator means for activating said actuator, said actuator means reciprocates in an upward and downward motion relative to the interior of said fluid collection chamber when activated, whereby the upward motion expands the volume of said collection chamber to provide a negative pressure in said fluid collection chamber relative to the pressure of said target whereby the negative pressure causes the fluid to be transported from the target into said fluid collection chamber.

41. A fluid transport apparatus for infusing fluid into a target, said fluid transport apparatus comprising:

at least one fluid dispenser chamber having a target wall and a distal wall opposite of said target wall, whereby said target wall is adapted for being mated against the target while said transport apparatus is in use;

an actuator means that is in mechanical communication with said distal wall, said actuator means reciprocates when activated;

at least one cutting device attached to said target wall of said fluid dispenser chamber and extending away from said fluid dispenser chamber, each such cutting device having a passage for transporting fluid there through; and a power supply operatively connected to said actuator means for activating said actuator, said actuator means reciprocates in an upward and downward motion relative to the target when activated, whereby the upward motion reduces the volume of said fluid dispenser chamber to provide a positive pressure in said fluid dispenser chamber relative to the pressure of said target whereby the positive pressure causes the fluid to be transported from said fluid dispenser chamber into the target.

42. The apparatus of claim 41, further comprising:

a fluid valve means for each of said respective cutting devices disposed at the attachment end of said cutting devices, said fluid valve means allows the flow of fluid into the target and prevents any fluid from exiting back into said fluid dispenser chamber.

43. A fluid transport apparatus for withdrawing target fluid from a target, and infusing storage fluid into the target said fluid sport apparatus comprising:

at least one fluid collection chamber having a collection target wall and a collection distal wall opposite of said collection target wall, a collection side wall that connects said collection distal wall with said collection target wall, whereby said collection target wall is adapted for being mated against the target while said transport apparatus is in use;

at least one fluid dispenser chamber having a storage target wall and a storage distal wall opposite of said storage target wall, a storage side wall that is proximate to or integral with said collection side wall so as to connect said storage distal wall with said storage target wall, thereby forming a generally common side wall defined by said side walls being adjacent or integral with one another, and whereby said storage target wall is adapted for being mated against the target while said transport apparatus is in use;

an actuator means that is in mechanical communication with said common side wall, said actuator means reciprocates when activated;

at least one cutting device attached to said target wall of each of said fluid collection chamber and fluid dispenser chamber and extending away from said respective chambers, each such cutting device having a passage for transporting fluid there through; and a power supply operatively connected to said actuator means for activating said actuator, said actuator means reciprocates in an upward and downward motion relative to the interior of said respective chambers when activated, whereby the upward motion contracts the volume of said fluid dispenser chamber to provide a positive pressure in said fluid dispenser chamber relative to the pressure of said target, whereby the positive pressure causes the fluid to be transported from said fluid dispenser chamber into the target, and whereby the upward motion expands the volume of said collection chamber to provide a negative pressure in said fluid collection chamber relative to the pressure of said target whereby the negative pressure causes the fluid to be transported from the target into said fluid collection chamber.

44. A fluid transport apparatus for withdrawing fluid from a target, whereby the target has target passages extending therein, said fluid transport apparatus comprising:

at least one fluid collection chamber having a target wall and a distal wall opposite of said target wall, whereby said target wall is adapted for being mated against the target while said transport apparatus is in use;

an actuator means that is in mechanical communication with said distal wall, said actuator means reciprocates when activated;

at least one aperture disposed on said target wall of said fluid collection chamber so as to be aligned with the respective target passage when said target wall is mated against the taget, thereby forming a passage between the target passage and said target wall aperture for transporting fluid there through; and a power supply operatively connected to said actuator means for activating said actuator, said actuator means reciprocates in an upward and downward motion relative to the target when activated, whereby the upward motion expands the volume of said collection chamber to provide a negative pressure in said fluid collection chamber relative to the pressure of said target whereby the negative pressure causes the fluid to be transported from the target into said fluid collection chamber.

45. A fluid transport apparatus for withdrawing fluid from a target, whereby the target has target passages extending therein, said fluid transport apparatus comprising:

at least one air storage chamber having an intermediate wall and a distal wall opposite of said intermediate wall;

at least one fluid collection chamber having a wall that is defined by said intermediate wall, said collection chamber further including a target wall opposite of said intermediate wall, whereby said target wall is adapted for being mated against the target while said transport apparatus is in use;

an actuator means that is in mechanical communication with said distal wall, said actuator means reciprocates when activated;

at least one aperture disposed on said target wall of said fluid collection chamber so as to be aligned with the respective target passage when said target wall is mated against the target, thereby forming a passage between the target passage and said target wall aperture for transporting fluid there through; and a power supply operatively connected to said actuator means for activating said actuator means, said actuator means reciprocates causing said distal wall to reciprocate in an upward and a downward motion relative to the target when activated, whereby the upward motion expands the volume of said air storage chamber to provide a negative pressure in said air storage chamber and fluid collection chamber relative to the pressure of said target and whereby the negative pressure causes the fluid to be transported from the target into said fluid collection chamber.

46. A method of transporting fluid from a target using a fluid transport apparatus, said method comprising the steps of:

inserting at least one cutting device into said target wherein said cutting device comprises a passage for transporting fluid there through to a fluid collection chamber, said fluid collection chamber comprising a target wall that is adapted for being mated against the target while said transport apparatus is in use, said fluid collection chamber having a distal wall that is opposite said target wall; and applying a negative pressure in said fluid collection chamber, wherein the negative pressure causes the fluid to be transported or withdrawn from the target into said passages of said cutting devices and transported or withdrawn into said fluid collection chamber, wherein said application of negative pressure comprises the following steps:

expanding the volume of said fluid collecting chamber via a fluid valve means disposed on said target wall, wherein said volume expansion of said fluid collection chamber comprises the following steps:

activating an actuator means that is in mechanical or electrical communication with said distal wall, said actuator means reciprocates causing said distal wall to reciprocate in an upward and a downward motion relative to the target when activated, whereby the upward motion expands the volume of said fluid collection chamber to provide the negative pressure in said fluid collection chamber relative to the pressure of said target and whereby the negative pressure causes the fluid to be transported from said target into said fluid collection chamber.

47. A method of transporting fluid from a target using a fluid transport apparatus, said method comprising the steps of:

inserting at least one cutting device into said target wherein said cutting device comprises a passage for transporting fluid there through to a fluid collection chamber, said fluid collection chamber comprising a target wall that is adapted for being mated against the target while said transport apparatus is in use, said fluid collection chamber having an intermediate wall that is opposite said target wall; and applying a negative pressure in said fluid collection chamber, wherein the negative pressure causes the fluid to be transported or withdrawn from the target into said passages of said cutting devices and transported or withdrawn into said fluid collection chamber, wherein said application of negative pressure comprises the following steps:
   expanding the volume of an air storage chamber that is open to said fluid collection chamber via a fluid valve means disposed on said intermediate wall, said air storage chamber defined by said intermediate wall and a distal wall opposite said intermediate wall, wherein said volume expansion of said air storage chamber comprises the following steps:
      activating an actuator means that is in mechanical or electrical communication with said distal wall, said actuator means reciprocates causing said distal wall to reciprocate in an upward and a downward motion relative to the target when activated, whereby the upward motion expands the volume of said air storage chamber to provide the negative pressure in said air storage chamber and fluid collection chamber relative to the pressure of said target and whereby the negative pressure causes the fluid to be transported from said target into said fluid collection chamber.

* * * * *